(12) United States Patent
Ogawa et al.

(10) Patent No.: US 6,261,780 B1
(45) Date of Patent: Jul. 17, 2001

(54) QUANTITATIVE ANALYSIS OF BIOCHEMICAL COMPOUND UTILIZING ELECTROCHEMICAL REACTION

(75) Inventors: Masashi Ogawa, Tokyo; Shigeori Takenaka, Koga; Makoto Takagi, Fukuoka, all of (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/477,973

(22) Filed: Jan. 5, 2000

(30) Foreign Application Priority Data

Jan. 6, 1999 (JP) .................................................. 11-001111
May 24, 1999 (JP) .................................................. 11-143599

(51) Int. Cl.[7] ...................................................... C12Q 1/68
(52) U.S. Cl. .............................. 435/6; 435/91.1; 435/91.2; 435/183; 435/189; 435/287.2; 204/450; 536/23.1; 536/24.3; 536/24.33

(58) Field of Search .............................. 435/6, 91.1, 91.2, 435/183, 189, 287.2; 204/450; 536/23.1, 24.3, 24.33

Primary Examiner—Bradley L. Sisson
(74) Attorney, Agent, or Firm—Reed Smith LLP

(57) ABSTRACT

A method for quantitatively analyzing a biochemical compound such as glucose or cholesterol is performed by bringing the biochemical compound into contact with double stranded DNA fragments which are fixed onto a surface of an electrode at their one terminals and in which electrochemically active threading intercalators are intercalated, in an aqueous medium under application of electric potential to the electrode in the presence of an oxidase capable of oxidizing the biochemical compound and becoming a reduced oxidase, and detecting an electric current flowing between the electrode and another electrode placed in the aqueous medium.

8 Claims, 4 Drawing Sheets

QUANTITATIVE ANALYSIS OF BIOCHEMICAL COMPOUND UTILIZING ELECTROCHEMICAL REACTION

FIELD OF THE INVENTION

This invention relates to a method for quantitatively analyzing a biochemical compound utilizing electrochemcial reaction.

BACKGROUND OF THE INVENTION

Biochemical compounds such as glucose, cholesterol, urea nitrogen, uric acid, bilirubin, ammonia, hemoglobin, neutral fat, lactic acid, fructosylamino acid, and L-glycerolphosphoric acid are contained in various biological liquids or body fluids such as whole blood, plasma, serum, urine, lymph, and pulpal liquid. The quantitative analysis of the biochemical compound (i.e., analyte) in body fluids is of great value for diagnosis of patients suffering from various diseases.

Previously, the quantitative analysis of the analytes have been performed by a wet method or a dry method. The wet method generally comprises a color formation reaction between the analyte and a color-forming reagent or in the presence of the analyte in an aqueous medium. The dry method generally employs a strip or a multilayer analytical element containing a color-forming reagent. Each of these methods has each advantageous feature and therefore both are widely employed in diagnosis of patients who possibly suffer from various diseases. However, both methods have disadvantageous features in that it is not easy to obtain the test results quickly because the color formation reaction is involved, and further they show a relatively low sensitivity in analyzing an extremely small amount of analyte.

In order to obtain the test results more quickly and to analyze an extremely small amount of analyte with an increased sensitivity, and enzyme sensor such as glucose sensor has been developed. The analytical system of the glucose sensor comprises the step of oxidizing the target glucose with glucose oxidase to produce gluconic acid and hydrogen peroxide and the step of detecting the amount of the produced hydrogen peroxide by a hydrogen peroxide electrode to give an electric signal corresponding to the amount of the hydrogen peroxide. This system is disadvantageous from the view point of complicated apparatuses involved.

In Chemical Letters pp. 989–990 (1998), a report entitled "Enhanced Electron Transfer from Glucose Oxidase to DNA-Immobilized Electrode aided by Ferrocenyl Naphthalene Diimide, a Threading Intercalator" is published. The author includes the present inventors. The report discloses that a ferrocene-modified 1,4,5,8-naphthalene-tetracarboxydiimide bound to double stranded DNA by a threading intercalation mode, enhanced the electron transfer between glucose oxidase and a DNA-immobilized electrode. This report, however, does not teach that the discovery may be utilized in analytical methods.

Recently, it has been desired to provide a method of quantitative analysis of analytes in body fluids which gives the analytical results more easily and more quickly using a simple apparatus.

SUMMARY OF THE INVENTION

Accordingly, it is an object of the invention to provide a method for quantitative analyzing analytes in body fluids which gives the analytical results quickly and easily using a simple apparatus.

The present invention resides in a method for quantitatively analyzing a biochemical compound which comprises bringing the biochemical compound into contact with double stranded DNA fragments which are fixed onto a surface of an electrode at their one terminals and in which electrochemically active threading intercalators are intercalated, in an aqueous medium under application of electric potential to the electrode in the presence of an oxidase capable of oxidizing the biochemical compound and becoming a reduced oxidase, and detecting an electric current flowing between the electrode and another electrode placed in the aqueous medium.

In the analytical method of the invention, examples of the biochemical compounds include glucose, cholesterol, lactic acid, fructosylamino acid and L-glycerolphosphoric acid, and examples of the oxidases include glucose oxidase, cholesterol oxidase, lactose oxidase, fructosylamino acid oxidase and L-glycerolphosphoric acid oxidase.

In the analytical method, the double stranded DNA fragments can be formed by combining, by hybridization, complementary DNA fragments with single stranded DNA fragments fixed onto the surface of electrode at their one terminals or by attaching separately prepared double stranded DNA fragments to the surface of electrode.

In the analytical method, the electrochemically active threading intercalator preferably is a compound showing oxidation-reduction activity, and more preferably is a compound having two chain groups at each terminal of which a ferrocene moiety is attached. The electrochemically active threading intercalator is present preferably in the aqueous medium in a concentration of 10 nM to 10 mM. The double stranded DNA fragments are fixed onto the electrode surface preferably in an amount of $10^{-11}$ to $10^{-10}$ mol. per 1 mm$^2$ of the electrode surface.

DETAILED DESCRIPTION OF THE INVENTION

Figure 1:
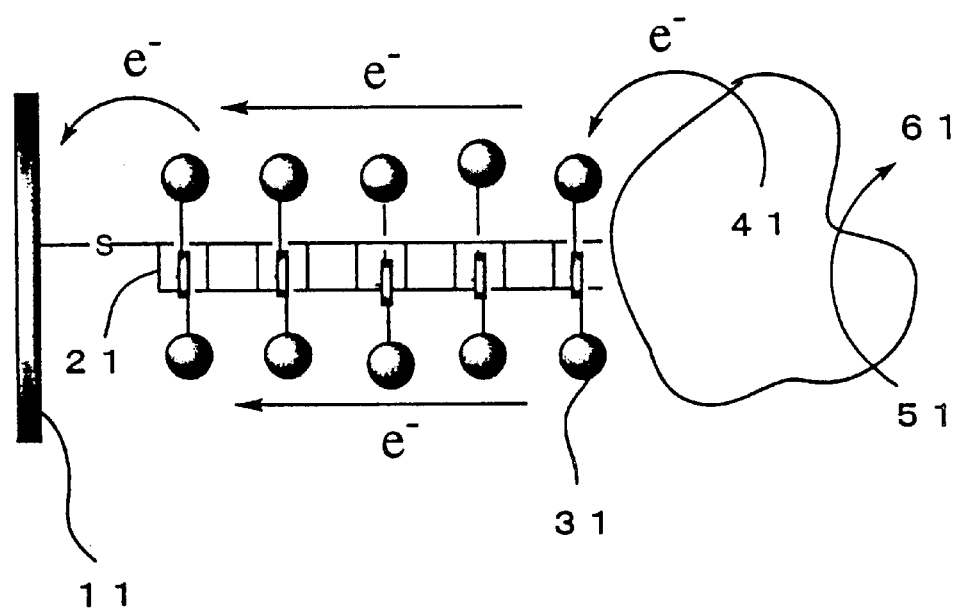
FIG. 1 schematically shows a mechanism of transmitting electrons produced by reduction of oxidase to a DNA fragment-immobilized electrode via electrochemically active threading intercalators intercalated into the double-stranded DNA fragment.

The mechanism supporting the analytical method of the invention is schematically shown in FIG. 1. A plural number of electrochemically active intercalators 31 are intercalated into a double-stranded DNA fragments 21 fixed on an electrode 11 at their one ends. The intercalators 31 are placed in the double-stranded DNA fragments 21 under such conditions that their terminal moieties such as ferrocene moieties protrude from the side lines of the DNA fragments 21 and are aligned in the longitudinal direction of the double-stranded DNA fragments 21. The aligned terminal groups serve for transmitting electrons which are produced by the oxidative reaction between an analyte such as glucose and an oxidase such as glucose oxidase. In the reaction, the oxidase is changed into a reduced oxidase by producing an electron.

It is discovered by the present inventors that the electric current transmitted from the reaction system to the electrode through the aligned terminal moieties (e.g., ferrocene moieties) varies proportionally with the amount of analyte (e.g., glucose) when an enough amount of oxidase is present. As a result of further study, it is confirmed that the electron-transmitting mechanism in the electrochemically active intercalators intercalated into double-stranded DNA fragments immobilized on an electrode can be utilized for quantitative analysis of an extremely small amount of a biochemical compound (i.e., analyte).

Figure 2:
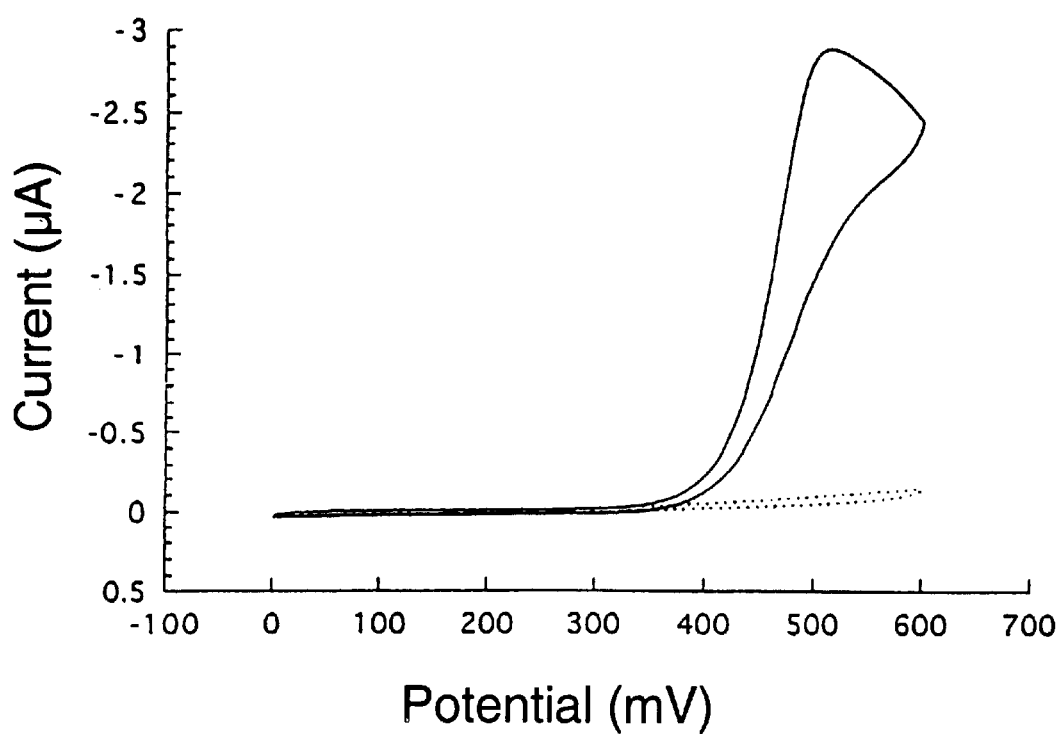
FIG. 2 shows two cyclic voltammograms, one of which (solid curve) is given in the presence of glucose and glucose oxidase, and another of which (dotted curve) is given in the absence of glucose and glucose oxidase.

The above-mentioned mechanism is more easily understandable from the two cyclic voltammograms of FIG. 2, in which the solid curve is given in the presence of glucose and glucose oxidase, and the dotted curve is given in the absence of glucose and glucose oxidase. Comparison between the two voltammograms indicate that an electric current flowing along the aligned terminal moieties of the threading intercalators is kept essentially at the same level in the absence of analyte and oxidase, while an applied electric potential is increased, but in the presence of analyte and oxidase, an electric current flowing along the aligned terminal moieties of the threading intercalators sharply increases when an applied electric potential is increased beyond a certain level. Accordingly, it is concluded that the sharp increase of the detected current is caused by the presence of the reaction system between the analyte and oxidase.

Figure 3:
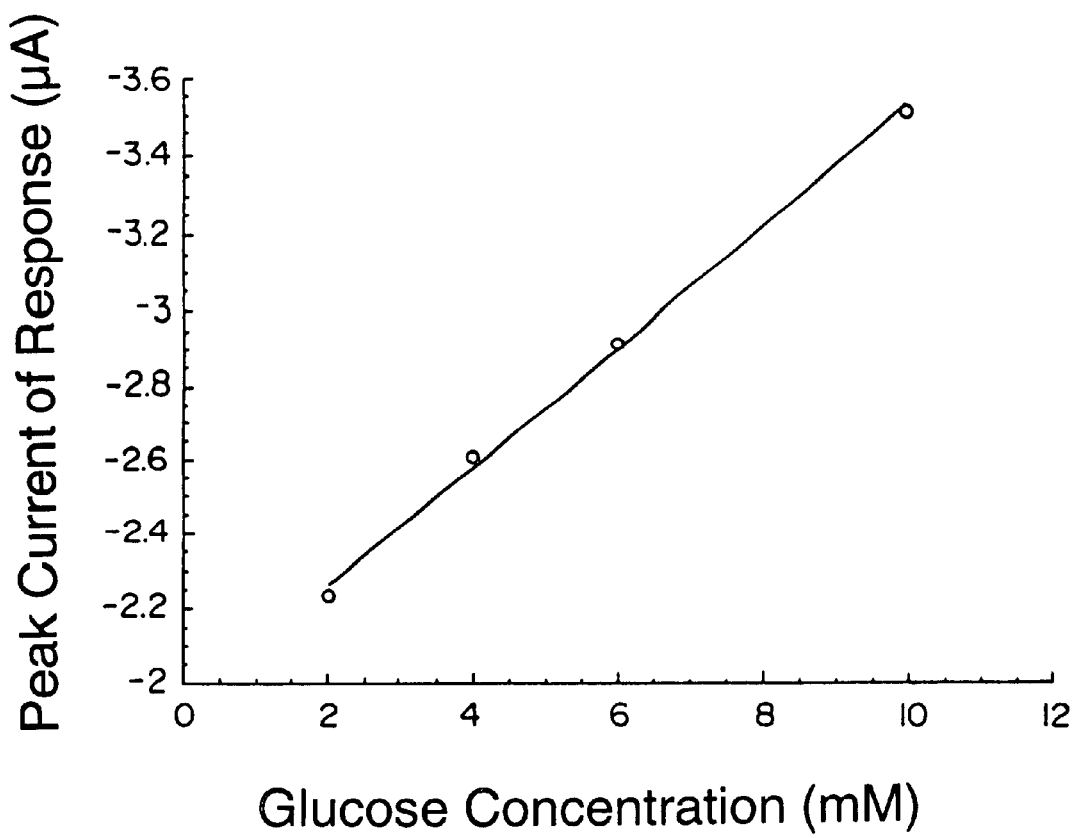
FIG. 3 shows a calibration curve indicating a relationship between a glucose concentration and a peak current of response.
Figure 4:
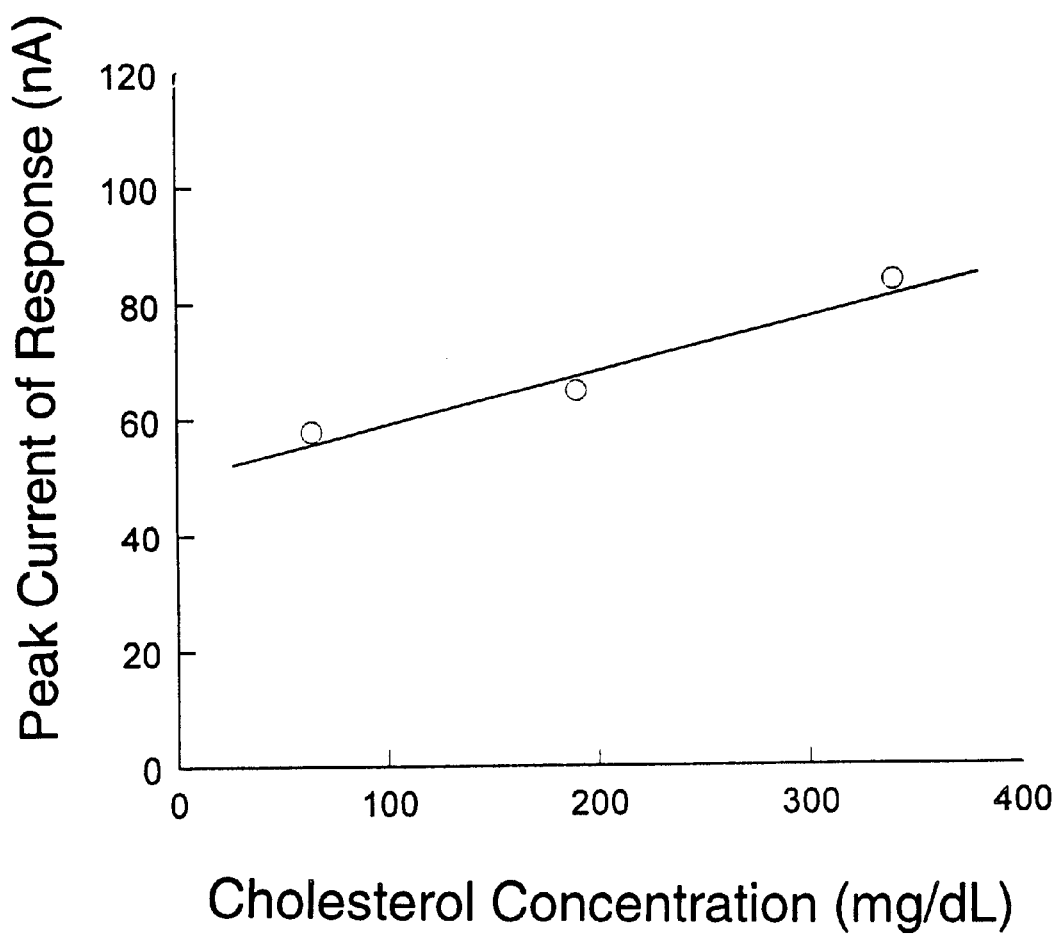
FIG. 4 shows a calibration curve indicating a relationship between a cholesterol concentration and a peak current of response.

FIG. 3 illustrates a calibration curve indicative of a relationship between a glucose concentration and a peak current of response, and FIG. 4 illustrates a calibration curve indicative of a relationship between a cholesterol concentration and a peak current of response. Apparently, both calibration curves show good linearity.

Analytes and analytical means utilized in the analytical method of the invention are further described below.

The analytical method is performed by bringing the biochemical compound into contact with double stranded DNA fragments which are fixed onto a surface of an electrode at their one terminals and in which electrochemically active threading intercalators are intercalated.

Examples of the biochemical compounds (i.e., analytes) include glucose, cholesterol, lactic acid, fructosylamino acid, and L-glycerolphosphoric acid. The analysis of other analytes also can be made, provided that an appropriate oxidase is present.

The electrode generally is in the form of a small chip and can be made of gold, glassy carbon, carbon, or other electroconductive materials. Plural electrode are arranged generally in two dimensional directions.

On the electrode, a number of double-stranded DNA fragments are immobilized by fixing one ends of the DNA fragments. The fixation of the DNA fragments onto the electrode may be made by forming a —S— bonding or an amide bonding between one terminal (i.e., 3'-terminal or 5'-terminal) of the DNA fragment and the surface of electrode. The formation of —S— bonding between one terminal of a DNA fragment and a surface of gold electrode is described in M. Maeda et al., Chem. Lett., pp. 1805–1808 (1994) and B. A. Connolly, Nucleic Acids Res., 13, 4484 (1985). The formation of amide bonding between one terminal of a DNA fragment and a surface of glassy carbon electrode is described in K. M. Millan et al., Analytical Chemistry, 65, 2317–2323 (1993).

The double-stranded DNA fragments immobilized on the electrode can be formed by fixing independently produced double-stranded DNA fragments onto a surface of electrode. Otherwise, a complementary single-stranded DNA fragment is combined with a single-stranded DNA fragment (i.e., probe DNA fragment) immobilized on a surface of electrode by hybridization so that a double-stranded DNA fragment can be formed on the surface of electrode.

The probe DNA fragment (i.e., a single stranded DNA fragment) can be obtained from DNA which is obtained by the steps of extraction from a living body, cleavage by restriction enzyme, separation by electrophoresis, and denaturation by heat-treatment or alkaline-treatment. The single stranded DNA fragment can be chemically synthesized. In any case, it is preferred that the single stranded probe DNA fragment is previously analyzed in its base sequence according to the known methods.

The hybridization is preferably carried out in the presence of the threading intercalator, which is preferably used in a concentration of several nM to several mM. The intercalator can accelerate the hybridization between the probe DNA fragment and a complementary DNA fragment and per se inserts into the bridging structure of the hybridized DNA fragment so that the hybridized DNA fragments is stabilized. Thus produced complex of the intercalator and the hybrid DNA fragment can be understood as a polymer having on its side a number of terminal moieties such as ferrocene moieties. Thus aligned terminal moieties serve to assist the electron transfer from the reduced oxidase to the electrode. When no hybridization occurs, the intercalator does not bind to the single stranded DNA fragment or is easily releasable from once-attached DNA fragment hybridized structure.

The electrochemically active threading intercalator preferably is a compound having an oxidation-reduction activity (i.e., redox activity) and easily enters into the matrix formed in the hybrid structure. Examples of the moieties showing the oxidation-reduction activity include ferrocene, catechol amine, metal-bipyridine complex, metal-phenanthroline complex, and biologen. Most preferred is ferrocene. The center portion of the intercalator may be naphthalene diimide, anthracene, or anthraquinone. The center portion and the ferrocene moieties are linked by an appropriate linking group.

Most preferred intercalator of the following formula can be synthesized by the reaction between ferrocene-carboxylic acid-hydroxysuccinimide ester with a corresponding imide derivative as described in S. Takenaka et al., J. Chem. Soc., Commun., 1111 (1998).

(NDIFc₂)

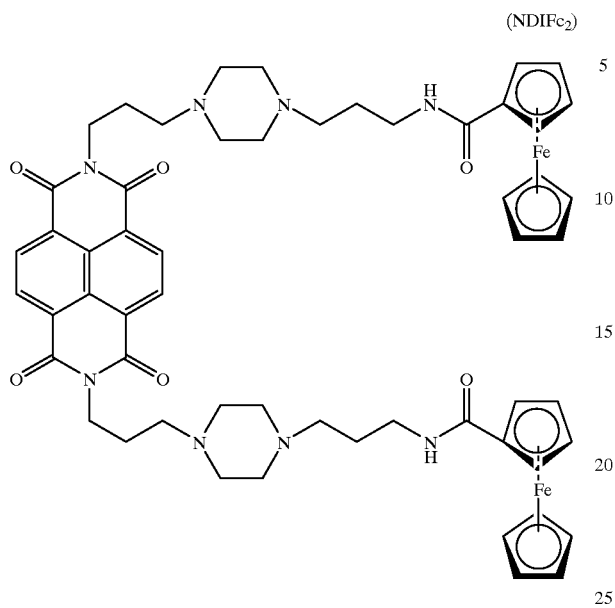

The following ferrocene-naphthalene diimide derivative is also preferred.

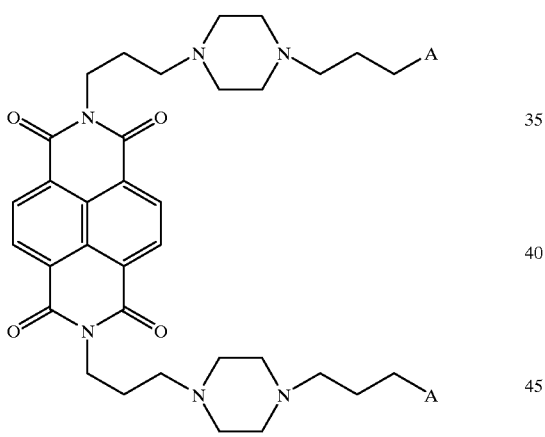

In the above formula, A can be one of the following ferrocene moieties:

(A1)

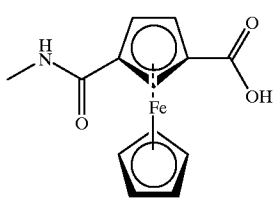

(A2)

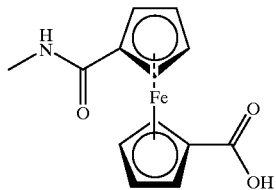

(A3)

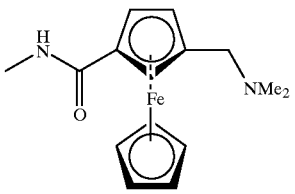

(A4)

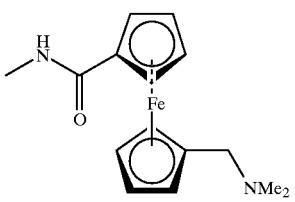

(A5)

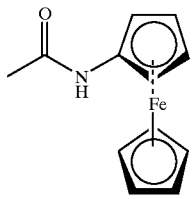

(A6)

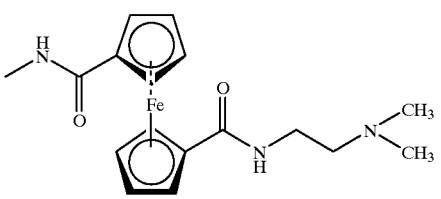

The electrochemically active threading intercalator contains a linker moiety which connects the moiety showing the redox activity and the central portion to be inserted into the matrix of the hybrid DNA. In the previously illustrated formula, the 1,4-dipropylpiperazine moiety is the linker moiety. The piperazine group can be replaced with a divalent quaternary amine. The compound having the divalent quaternary amine (which is illustrated below) serves as cation in an aqueous medium independently of it pH condition, and hence shows increase affinity to the hybrid DNA. The linker moiety can be replaced with any other appropriate moiety. Depending upon the structure of the linker moiety, the oxidation-reduction potential may vary.

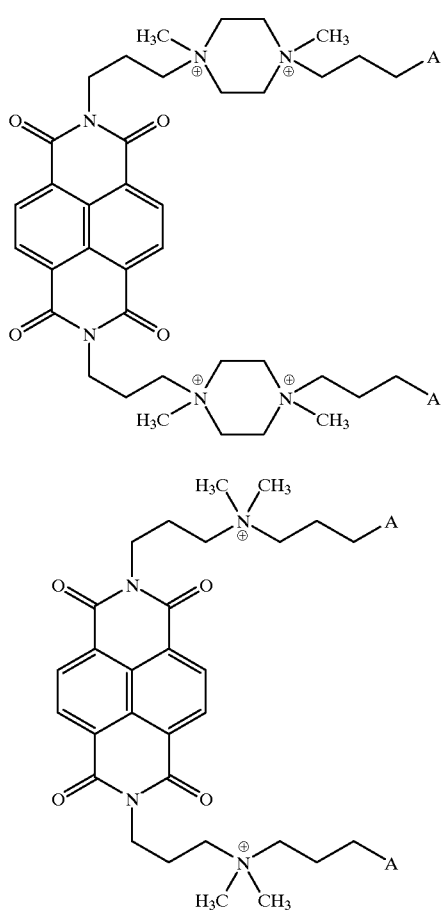

(NDIFc₂-1)

(NDIFc₂-2)

In the case that the above-illustrated naphthalene diimide derivative is employed as the intercalator, it enters the matrix of the hybrid DNA fragment by every two base moieties and densely bonded to the hybrid DNA fragment. Therefore, the ferrocene moieties are densely aligned along the longitudinal axis of the hybrid DNA fragment. Therefore, the naphthalene diimide derivative once incorporated into the hybrid DNA fragment is not easily released.

A sample DNA fragment which is converted into a single stranded DNA fragment by the conventional method is generally employed in a solution containing several $10^{-18}$ to several $10^{-10}$ molar concentration, preferably several $10^{-18}$ to several $10^{-12}$ molar concentration.

The oxidase can be reduced to release two electrons which are generated in the course of the reaction with an analyte in the presence of oxygen to give a reduced peroxide. Examples of the preferred oxidases include glucose oxidase, cholesterol oxidase, lactose oxidase, fructosylamino acid oxidase, and L-glycerolphosphoric acid oxidase, which are employed in combination with appropriate analytes.

Preferred glucose oxidase is derived from *Aspergillus niger* or *Penisillim notatum*. Preferred cholesterol oxidase is derived from *Nocardia erythroporis,* Brevibacterium, Pseudomonas, or Mycobacterium. Preferred lactase oxidase is derived from *Aerococcus viridans,* or Pediococcus sp.

After the hybridization is complete, the electrode is preferably washed out to remove a free intercalator.

The reaction between the probe DNA and a sample DNA can be determined by measuring electric current to the electrode. The measurement of electric current can be performed in any conventional methods, such as cyclic voltammetry, differential pulse voltammetry, and potentiostat.

In the high sensitive DNA detection system according to the invention, the electric current of 20 to 100 times as much as that of the conventional system employing no oxidase-substrate combination can be detected. Moreover, the adjustment of a buffer solution or a scanning speed can give an electric current or more than 100 times as much as that of the conventional system.

EXAMPLE 1

(1) Preparation of electrode having a fixed probe DNA

On a gold electrode (surface area: 2.25 mm²) was spotted 2 μL of an aqueous solution containing 150 pico mol. of 20mers (dT₂₀) of thymidine having a mercapto moiety at its 5'-terminal (see below):

5'-TTTTTTTTTTTTTTTTTTTT-3' to fix the probe DNA fragment onto the gold electrode. The probe DNA fragment was fixed on the gold electrode in an amount of 20 pico mol. of dT₂₀ per 2 mm² of the surface area of the electrode. The synthesis and fixation of dT₂₀ were carried out in the manner as described in Japanese Patent Provisional Publication H9-288080.

(2) Preparation of ferrocene-containing threading intercalator

The preparation of the following ferrocene-containing threading intercalator (NDIFc₂) was done in the manner described in the above-mentioned patent publication.

(NDIFc₂)

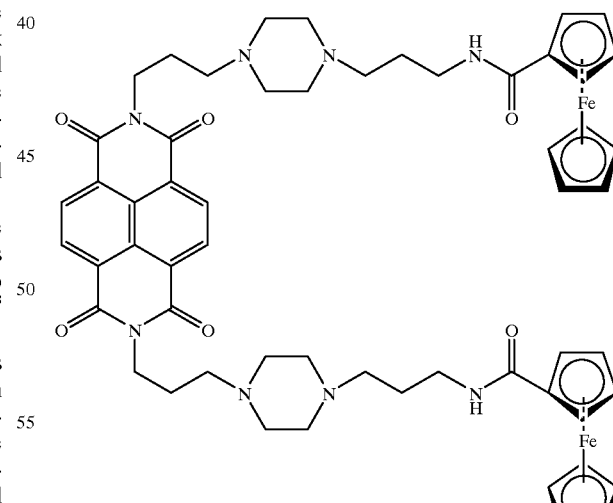

(3) Preparation of Sample DNA

A 20mers of adenine (dA₂₀) represented by the following formula was prepared in the manner described in the above-mentioned patent publication:

5'-AAAAAAAAAAAAAAAAAAAA-3'

(4) Formation of double-stranded DNA fragments on the electrode

In a mixture of $dA_{20}$ obtained in (3) above (286 pico mol.) and the ferrocene-containing threading intercalator (50 μM) in a mixture of 0.1M aqueous acetic acid-potassium acetate solution (pH 5.6) and 0.1M aqueous potassium chloride solution was placed the gold electrode on which $dT_{20}$ was fixed, for 20 minutes at 25° C. for performing incubation. Thus incubated electrode was taken out, and washed for 5 seconds with an aqueous 0.1 M sodium dihydrogen phosphate/disodium hydrogen phosphate solution (pH 7.0), to remove a free intercalator, and an unreacted $dA_{20}$.

(5) Preparation of calibration curve

The gold electrode having the double-stranded DNA fragments on its surface, a platinum electrode and a silver/silver chloride referential electrode were immersed in a solution of glucose (10 mM) and glucose oxidase (200 U, derived from *Aspergillus niger*, available from Wako Corporation) in an aqueous 0.1 M sodium dihydrogen phosphate/disodium hydrogen phosphate/0.1 M potassium chloride solution (pH 7.0) to form tri-electrode system. Then, cyclic voltammometry was performed to give a cyclic voltammogram by scanning at 25 mV/sec at an electric potential of 514 mV. The obtained voltammogram is shown in FIG. 2 in the form of a solid curve.

For comparison, the above-mentioned procedures were repeated except for employing neither glucose nor glucose oxidase to obtain a voltammogram. The voltammogram is shown in FIG. 2 in the form of a dotted curve.

(6) Comparison of voltammograms

FIG. 2 indicates that the electric current increased in the presence of a combination of glucose and glucose oxidase (shown in the form of a full line) was $-2.9$ μA at an electric potential of 514 mV, while the corresponding current was $-0.1$ μm. This means that the electric current in the analytical system according to the invention is increased 29 times as much as that of not utilizing the combination of glucose and glucose oxidase.

EXAMPLE 2

The procedure of Example 1-(5) was repeated except for changing the glucose concentration into 2 mM, 4 mM, or 6 mM, to obtain cyclic voltammograms for each glucose concentration. The peak electric currents at 480 mV of the voltammograms determined in these procedure as well as in Example 1-(5) are shown in FIG. 3 to prepare a calibration curve. Apparently, a calibration curve showing satisfactory linearity is given in the range of 2 to 10 mM. The peak electric current is determined by reducing the measured base electric current (in the absence of glucose and glucose oxidase) from the measured peak electric current (in the presence of glucose and glucose oxidase).

The linearity of the calibration curve is described by the following equation:

$$Y = -1.9487 - 0.15823 \times (X)$$

[X is a glucose concentration (mM) and Y is a peak current (μA)]

The correlation coefficient is 0.99867.

The above-mentioned results means that the analytical method of the invention is appropriately employable in quantitatively determining the glucose concentration in a human blood in the range of 4.2 to 5.6 mM, which is a normal range of glucose concentration of a normal body.

EXAMPLE 3

The procedure of Example 1-(5) was repeated using cholesterol (64 mg/dL, 190 mg/dL, and 340 mg/dL) and cholesterol oxidase (20 U, originating from *Nocardia erythroporis*, available from Wako Corporation), to obtain cyclic voltammograms for each cholesterol concentration. The cyclic voltammetry was performed to give a cyclic voltammogram by scanning at 1 mV/sec. The obtained calibration curve is shown in FIG. 4.

Apparently, a calibration curve showing satisfactory linearity is given in the range of 64 to 340 mg/dL. The peak electric current is determined by reducing the measured base electric current (approximately $-0.1$ μA, in the absence of cholesterol and cholesterol oxidase) from the measured peak electric current (in the presence of glucose and glucose oxidase).

The above-mentioned results mean that the analytical method of the invention is appropriately employable in quantitatively determining the cholesterol concentration in a human blood in the range of 120 to 220 mM, which is a normal range of cholesterol concentration of a normal body.

What is claimed is:

1. A method for quantitatively analyzing a biochemical compound comprising
    bringing the biochemical compound into contact with double stranded DNA fragments which are fixed onto a surface of an electrode at their one terminals and in which electrochemically active threading intercalators are intercalated, in an aqueous medium under application of electric potential to the electrode in the presence of an oxidase capable of oxidizing the biochemical compound and becoming a reduced oxidase, and
    detecting an electric current flowing between the electrode and another electrode placed in the aqueous medium by cyclic voltammetry, linear sweep voltammetry, differential pulse voltammetry or potentiostat;
    wherein the electrochemically active threading intercalator is present in the aqueous medium in a concentration of 10 nM to 10 mM.

2. The method of claim 1, wherein the biochemical compound is glucose, cholesterol, lactic acid, fructosylamino acid or L-glycerolphosphoric acid, and the oxidase is glucose oxidase, cholesterol oxidase, lactose oxidase, fructosylamino acid oxidase or L-glycerolphosphoric acid oxidase, respectively.

3. The method of claim 1, wherein the double stranded DNA fragments are formed by combining, by hybridization, complementary DNA fragments with single stranded DNA fragments fixed onto the surface of electrode at their one terminals or by attaching separately prepared double stranded DNA fragments to the surface of electrode.

4. The method of claim 1, wherein the electrochemically active threading intercalator is a compound showing oxidation-reduction activity.

5. The method of claim 4, wherein the electrochemically active threading intercalator is a compound having two chain groups at each terminal of which a ferrocene moiety is attached.

6. The method of claim 1, wherein the double stranded DNA fragments are fixed onto the electrode surface in an amount of $10^{-11}$ to $10^{-10}$ mol. per 1 $mm^2$ of the electrode surface.

7. The method of claim 1, wherein the biochemical compound of glucose, the oxidase is glucose oxidase, and the glucose is present in the aqueous medium in a concentration of 1 to 35 mM.

8. The method of claim 1, wherein the biochemical compound is cholesterol, the oxidase is cholesterol oxidase, and the glucose is present in the aqueous medium in a concentration of 1 to 500 mM.

* * * * *